United States Patent [19]

Slater

[11] Patent Number: 4,878,486
[45] Date of Patent: Nov. 7, 1989

[54] DISPOSABLE COVER ARRANGEMENT FOR LARYNGOSCOPES AND THE LIKE

[76] Inventor: William M. Slater, 6 N. Buys, Muskegon, Mich. 49445

[21] Appl. No.: 72,600

[22] Filed: Jul. 13, 1987

[51] Int. Cl.$^4$ ............................................. A61B 1/06
[52] U.S. Cl. .................................. 128/110; 206/438; 53/292
[58] Field of Search ....................... 128/3, 4, 6, 10, 11, 128/7, 9, 15, 16, 17; 53/585, 292; 206/438, 829; 383/63

[56] References Cited

U.S. PATENT DOCUMENTS

| | | |
|---|---|---|
| 2,797,684 | 7/1957 | Moore . |
| 2,913,030 | 11/1959 | Fisher ................................ 383/63 |
| 3,326,208 | 6/1967 | Held . |
| 3,426,749 | 2/1969 | Jephcott . |
| 3,949,740 | 4/1976 | Twentier . |
| 4,201,199 | 5/1980 | Smith . |
| 4,406,280 | 9/1983 | Upsher . |
| 4,492,220 | 1/1985 | Hayes .................................. 128/17 |
| 4,570,614 | 2/1986 | Bauman . |
| 4,579,108 | 4/1986 | Bauman .............................. 128/10 |
| 4,583,527 | 4/1986 | Musicant et al. . |
| 4,638,792 | 1/1987 | Burgin . |
| 4,646,722 | 3/1987 | Silverstein .......................... 128/4 |
| 4,721,097 | 1/1988 | D'Amelio ............................ 128/4 |

Primary Examiner—Edward M. Coven
Assistant Examiner—Mark S. Graham
Attorney, Agent, or Firm—Price, Heneveld, Cooper, DeWitt & Litton

[57] ABSTRACT

A disposable cover is provided for laryngoscopes and the like of the type having an elongate blade with a contoured, channel-shaped guide surface on which an associated light source is mounted to facilitate inserting an endotracheal tube into the air passageway of a patient. The disposable cover comprises a sheath having a sterile exterior surface, and a closed interior surface defining a hollow cavity shaped to receive therein and envelope the laryngoscope blade. The sheath has an open end through which the laryngoscope blade is inserted into the cavity of the sheath. The sheath is readily flexible so that an associated portion of the same can be conformed to the contoured guide surface of the laryngoscope blade. Being constructed from a light-transmitting material, the sheath permits light waves emitted from the light source to pass through the sheath, and illuminate the air passageway of the patient. The sheath is selectively fitted on the laryngoscope blade in a manner which securely retains the associated portion of the sheath closely against the contoured guide surface of the laryngoscope blade, such that the view along the air passageway of the patient remains wholly unobstructed during insertion of the endotracheal tube, yet permits the sheath to be manually stripped from the laryngoscope blade for disposal after a single use.

21 Claims, 3 Drawing Sheets

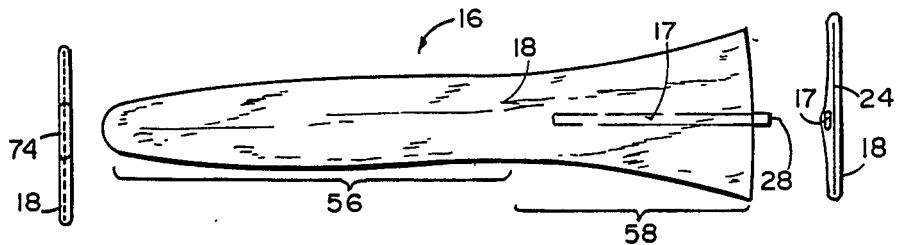
FIG. IA  FIG. I  FIG. IB
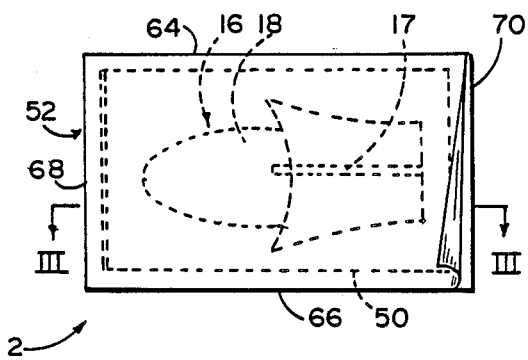
FIG. 2
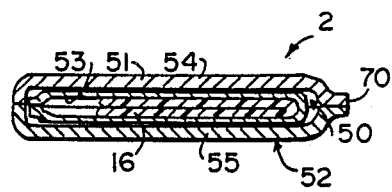
FIG. 3
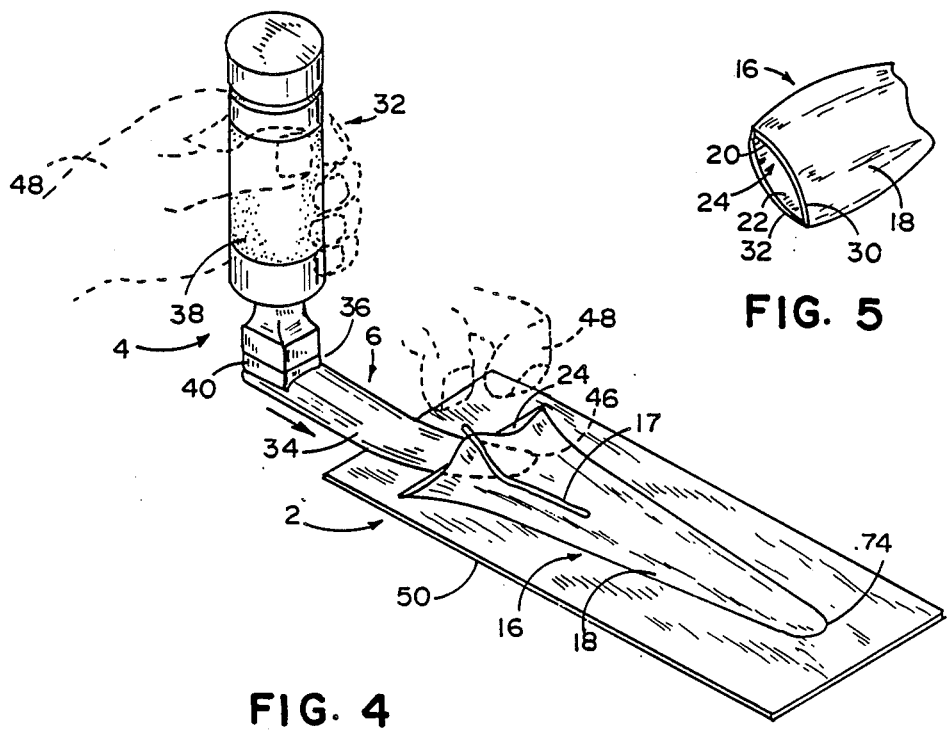
FIG. 4
FIG. 5

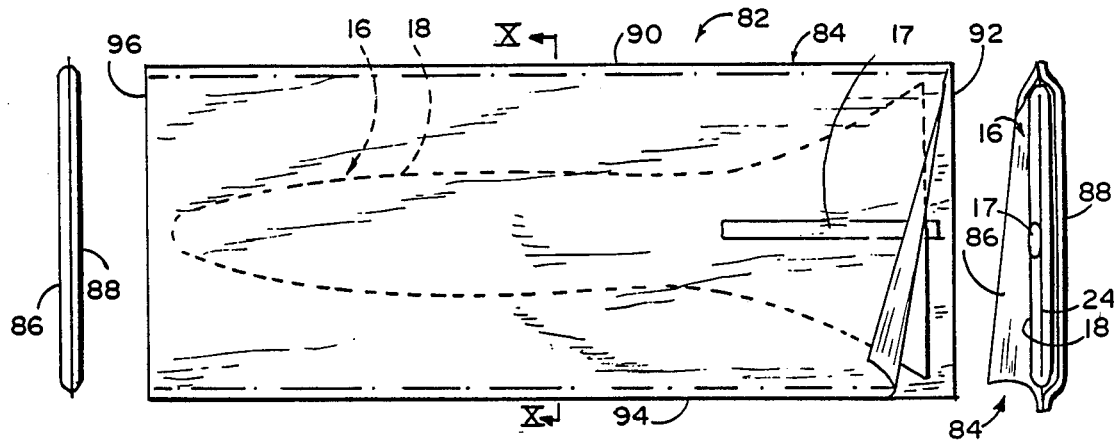
FIG. 9A  FIG. 9  FIG. 9B
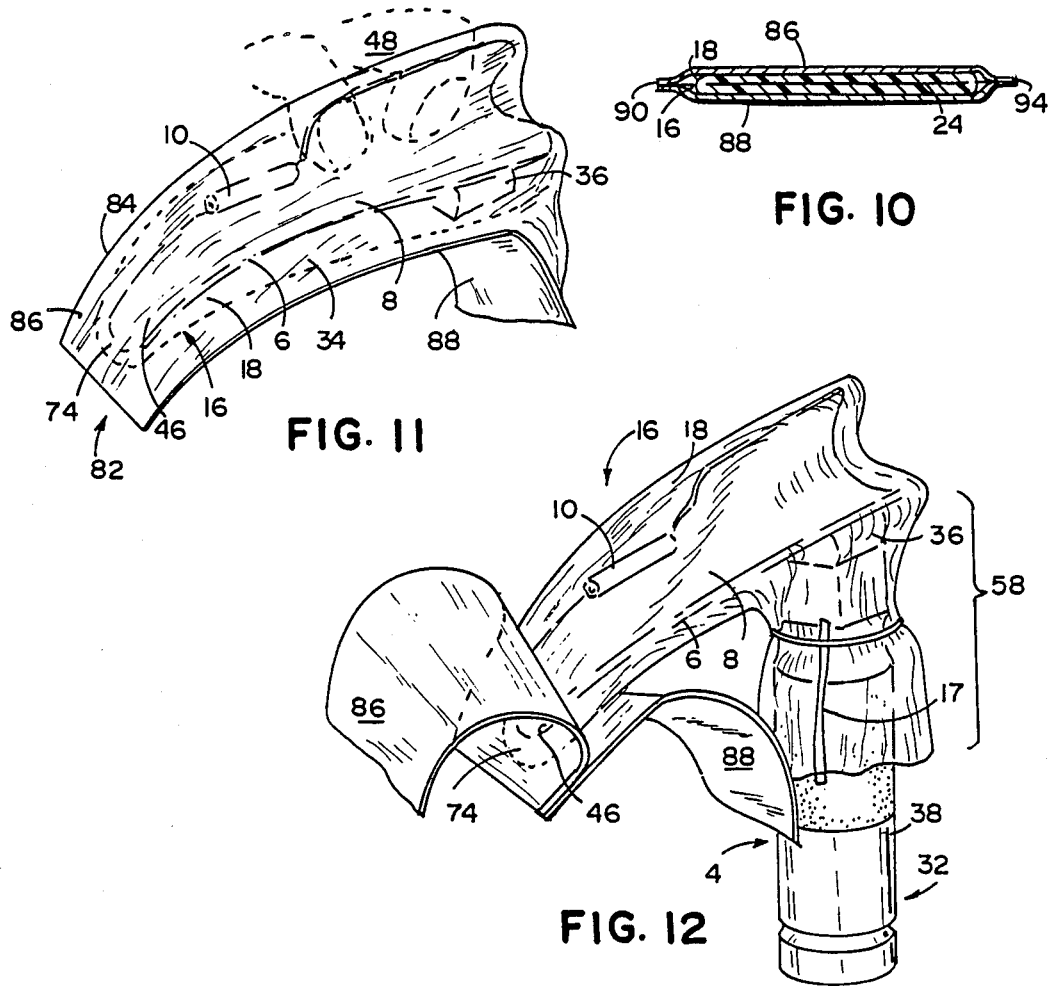
FIG. 10
FIG. 11
FIG. 12

DISPOSABLE COVER ARRANGEMENT FOR LARYNGOSCOPES AND THE LIKE

BACKGROUND OF THE INVENTION

The present invention relates to medical and surgical instruments, and in particular to disposable covers for laryngoscope blades, and the like.

When anesthetized, the human body tends to function somewhat irregularly. For instance, the air passageway may close up, and stomach acid may enter the lungs. To avoid this situation, and protect the lungs from stomach acid, an endotracheal tube is normally inserted into the patient's air passageway with the aid of a device which is typically used to examine the larynx, namely a laryngoscope. A conventional laryngoscope comprises a cylindrically shaped handle or housing with a detachable, elongate blade. The blade is usually hingedly attached to the laryngoscope housing at a contact point, and has either a C-shaped or L-shaped lateral cross-sectional shape, with inside and outside surfaces. The outside surface is shaped to conform to the interior surfaces of the patient's throat, and to facilitate lifting the patient's tongue, upon insertion of the blade into the patient's mouth and throat. The inside surface of the blade defines a space, which includes a guide surface, through which the physician can sight down into the patient's throat. The blade has a light located adjacent its outer end to assist in viewing the larynx, and a rounded tip to help move the epiglottis to facilitate the insertion of an endotracheal tube, without undue trauma to the patient's throat.

In the past, not much concern has been given to sterilizing blades of laryngoscopes, including the blade portion of the laryngoscope which is inserted into the throat of the patient. Considering the significant number of patients that an anesthesiologist might serve each day, possibly 40 per day, the lack of sterilization of the laryngoscope blades might possibly lead to cross-contamination among patients, at least under some circumstances. This situation, coupled with the present fear of contracting serious diseases such as AIDS, hepatitis, herpes, etc. during surgery, has given rise to a demand for the use of sterile equipment whenever possible. Frequent sterilization of the laryngoscope blade is not feasible, since to do so would be time-consuming and very inconvenient. While there are methods for manually sterilizing laryngoscope blades, such methods tend to be time-consuming in application and burdensome for the practitioner who typically does not have time to wait. Quick sterilization of laryngoscope blades through conventional methods such as autoclaving is out of the question, since the standard laryngoscope blade includes a delicate, light assembly mounted on the blade itself. The use of a resterilizable blade cover would still pose a hardship to the anesthesiologist or anesthetist in light of the many covers that would have to be sterilized each day, and the possibility of incomplete sterilization. Accordingly, there is a demand in the medical field for a cover that is completely sterile, and can be used on all different types of commonly-used laryngoscope blades with varying shapes, and can be disposed of after a single use.

SUMMARY OF THE INVENTION

One aspect of the present invention is to provide a disposable cover for laryngoscopes and the like of the type having an elongate blade with a contoured, channel-shaped guide surface on which an associated light source is mounted to facilitate inserting an endotracheal tube into the air passageway of a patient. The disposable cover comprises a sheath having a sterile exterior surface, and a closed interior surface defining a hollow cavity shaped to receive therein and envelop the laryngoscope blade. The sheath has an open end through which the laryngoscope blade is inserted into the cavity of the sheath. The sheath is readily flexible so that an associated portion of the same can be conformed to the contoured guide surface of the laryngoscope blade. Being constructed from a light-transmitting material, the sheath permits light waves emitted from the light source to pass through the sheath, and illuminate the air passageway of the patient. The sheath is selectively fitted on the laryngoscope blade in a manner which securely retains the associated portion of the sheath closely against the contoured guide surface of the laryngoscope blade, such that the view along the air passageway of the patient remains wholly unobstructed during insertion of the endotracheal tube, yet permits the sheath to be manually stripped from the laryngoscope blade for disposal after a single use.

In one example of the present invention, the sheath is constructed from two sheets of flexible plastic material, which are integrally fused together along two side edges and an end edge thereof to form the hollow cavity, with an unjoined end edge defining the open end into which the laryngoscope blade is inserted. A tube is attached to the interior of the sheath and provides communication between the hollow cavity of the sheath and a vacuum source. The sheath further comprises at least one integrally formed tacky surface for securely holding the sheath against the guide surface to define a portion of the fitting means. To avoid contamination of the sheath prior to use on the patient, a portion of the exterior surface of the sheath is adhesively mounted on a sterile, disposable cover sheet folded and packaged in a releasably sealed envelope such that upon withdrawing the cover sheet from the envelope and unfolding the cover sheet the open end of the sheath is exposed. Upon insrting the blade of the laryngoscope into the hollow cavity of the sheath, the sheath can be easily pulled away from the cover sheet, and the associated portion of the sheath can be conformed to the guide surface of the blade by applying a vacuum source to the tube communicating from the sheath's interior surface. A portion of the sheath, which is not conformed to the guide surface after covering the blade with the sheath, is affixed to the laryngoscope. The nonconformed portion can be used to invert the associated portion of the sheath, which may be contaminated during use on the patient, upon removal of the sheath.

The principal objects of the present invention are to provide a sterile disposable cover that is readilY adaptable to larYngoscope blades of varying shapes and sizes. The cover includes a flexible sheath of light-transmitting material that can be closely conformed against the contoured guide surface of the blade in a matter of seconds such that the view along the air passageway of the patient remains wholly unobstructed during intubation of the same. Because of its flexibility, the cover need not be premolded for individual blade types, and since the sheath is intended for single use, problems associated with resterilization are eliminated. The cover has an uncomplicated construction and is pàrticularly economical to manufacture, efficient to use, easy to ship and well adapted for the proposed use.

These and other features, advantages and objects of the present invention will be further understood and appreciated by those skilled in the art by reference to the following written specification, claims and appended drawings.

BRIEF DESCRIPTION OF THE DRAWINGS

FIG. 1 is a top plan view of a sheath portion of a disposable cover embodying the present invention;

FIG. 1A is a left-hand end view of the sheath;

Figure 6:
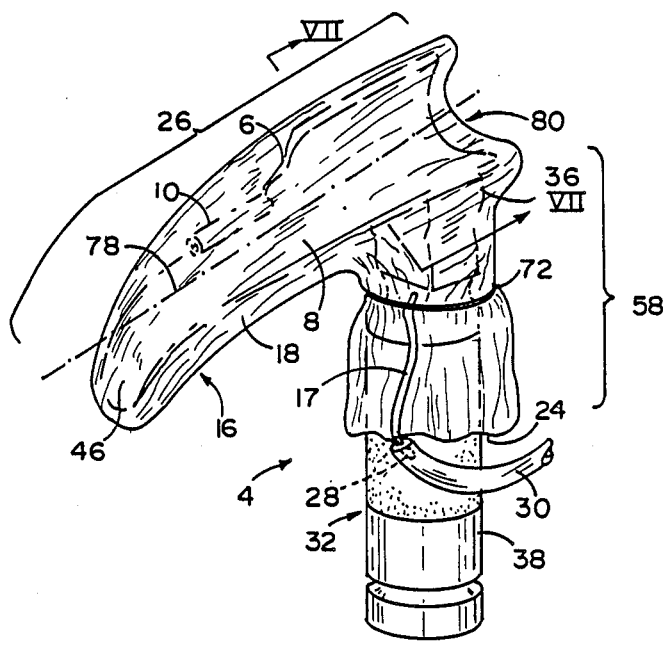
Figure 7:
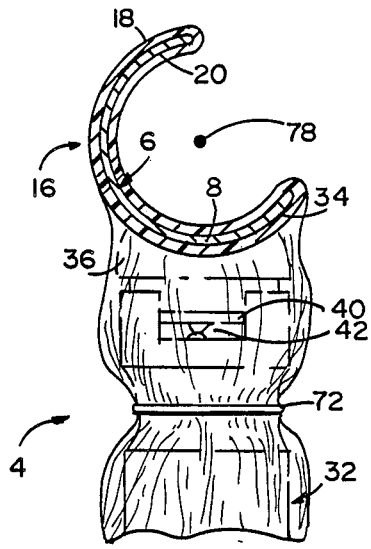
Figure 8:
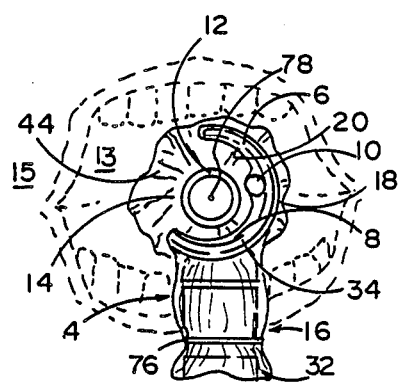

FIB. 1B is a right-hand end view of the sheath;

FIG. 2 is a top plan view of the cover, including an envelope encasing the sheath mounted on the cover sheet, with an end portion of the envelope pulled partially open;

FIG. 3 is an enlarged, transverse, cross-sectional view of the cover, taken along plane III—III of FIG. 2;

FIG. 4 is a fragmentary perspective view of the cover in a partially open condition, ready for positioning an associated laryngoscope blade;

FIG. 5 is a fragmentary view of a partially opened sheath;

FIG. 6 is a perspective view of a laryngoscope with the sheath conformed to the laryngoscope blade, and the cover sheet being stripped away from the exterior surface of the sheath;

FIG. 7 is a transverse, cross-sectional view of the cover and laryngoscope blade taken along plane VII—VII of FIG. 6;

FIG. 8 is a transverse, cross-sectional view of the cover and laryngoscope blade demonstrating the use of the covered laryngoscope blade to intubate the air passageway of a patient; and FIG. 9 is a top plan view of an alternative embodiment of the cover, including an alternative envelope encasing the sheath with an end portion of the alternative envelope pulled partially open;

FIG. 9A is a left-hand end view of an alternative embodiment of the cover;

FIG. 9B is a right-hand end view of an alternative embodiment of the cover;

FIG. 10 is an enlarged, transverse, cross-sectional view of the alternative embodiment of the cover, taken along plane X—X of FIG. 9;

FIG. 11 is a fragmentary, perspective view of the laryngoscope blade covered by the alternative embodiment of the cover; and FIG. 12 is a perspective view of a laryngoscope with the sheath conformed to the laryngoscope blade, and the alternative envelope being stripped away from the exterior surface of the sheath.

DETAILED DESCRIPTION OF THE PREFERRED EMBODIMENTS

For purposes of description herein, the terms "upper," "lower," "right," "left," "rear," "front," "vertical," "horizontal" and derivatives thereof shall relate to the invention as oriented in FIG. 7. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions, and other physical characteristics relating to the embodiments disclosed herein are not to be considered as limiting, unless the claims by their language expressly state otherwise.

Cover 2 including cover sheet 50, with sheath 16 mounted thereon, is applied to laryngoscope 4 as illustrated in FIG. 4. Laryngoscope 4 (FIGS. 6 and 7) comprises a blade 6 and holder 32. Laryngoscope blade 6 comprises guide surface 8, light source 10, exterior blade surface 34 and clamping member 36. The guide surface 8, exterior surface 34 and clamping member 36 are composed of a suitable metal, such as stainless steel. While plastic materials could be used to form blade 6, use of metal provides a more durable surface that is less likely to bend or crack upon manipulation within the mouth 13 of patient 15 (FIG. 8). Laryngoscope holder 32 includes handle 38, hinge 40 and an electrical system (not shown). The handle 38 which encases the electrical system is typically formed of a suitable metal, such as stainless steel, and the hinge 40 receives clamping member 36 of blade 6. The electrical system 60 typically includes a battery charged unit (not shown) and upon hingedly affixing clamping member 36 to holder 32 at a contact point 42 near hinge 40, light source 10 is illuminated. The laryngoscope blade 6, illustratively has a C-shaped lateral cross-sectional shape (FIG. 7), with concentric convex surface 34 and concave surface 8. The exterior, convex surface 34 is shaped to abut the interior surface of the patient's throat 44 (FIG. 8), and to lift the tongue of patient 15, upon insertion of the laryngoscope blade 6 into the mouth 13 of patient 15. The inside, concave surface 8 of laryngoscope blade 6 defines a cylindrical space through which the physician can sight to guide blade 6 down through the throat 44 of patient 15 (FIGS. 6 and 7). Blade 6 has a light source 10 adjacent to blade end portion 46 to view the larynx, and move the epiglottis, to facilitate the insertion of endotracheal tube 12 (FIG. 8); without undue trauma to the throat 44 of patient 15.

To use laryngoscope 4 (FIG. 8), exterior surface 34 of blade 6 is slid under the patient's tongue while mouth 13 is held open and laryngoscope 4 is manipulated via the handle 38. With the aid of light source 10, and by looking down guide surface 8, the epiglottis can be located. Using end portion 46, the epiglottis can be moved out of the way such that the endotracheal tube 12 can be inserted into the air passageway 14 of patient 15.

The reference numeral 2 generally designates a disposable cover 2 (FIG. 2) embodying the present invention. Disposable cover 2 is provided for medical and surgical instruments, such as the illustrated laryngoscope 4 (FIG. 4) of the type having an elongate blade 6 with a contoured, channel-shaped guide surface 8 on which an associated light source 10 is mounted to facilitate inserting an endotracheal tube 12 (FIG. 8) into the air passageway 14 of a patient 15. Disposable cover 2 (FIGS. 1-5) comprises a sheath 16 having a sterile exterior surface 18, a communication tube 17, and a closed interior surface 20 defining a hollow cavity 22 shaped to received therein and envelop laryngoscope blade 6. Sheath 16 has an open end 24 through which laryngoscope blade 6 is inserted into the cavity 22 of sheath 16. Sheath 16 is readily flexible so that an associated portion 26 of the same (FIG. 6) can be illustratively conformed to the contoured guide surface 8 of laryngoscope blade 6 by use of a vacuum source connected to communication tube 17. As illustrated in FIG. 1 communication tube 17 is attached to interior surface 20 of sheath 16 and communicates with the environment surrounding exterior surface 18 by way of suction end 28. The tube 17 is preferably composed of flexible plastic or rubber, and tube 17 has a circular or oblong cross section (FIG. 1B). The length of tube 17 must be great enough so that suction end 28 can closely receive a vacuum source tube 30 (FIG. 6) and yet still communicate with portion 26. Tube 17 is preferably mounted to the interior surface with an adhesive and exits sheath 16 at open end 24 (FIG. 6) and communicates with interior surface 20 of sheath 16 at a portion near open end 24. By mounting tube 17 between associated portion 26 and open end 24 suction can be evenly applied to associated portion 26 of sheath 16, and intubation of patient 15 can be performed without the presence of tube 17 in guide surface 8. In the preferred embodiment vacuum source tube 30 is applied to associated portion 26 of sheath 16 via communication tube 17, but alternatively subsequent to covering blade 6 and part of holder 32 with sheath 16 (FIG. 6) a vacuum source can be directly applied to associated portion 26 of sheath 16. The vacuum tube 30 is simply inserted into sheath 16 via open end 24 far enough to apply suitable suction to portion 26 causing portion 26 to be pulled down onto guide surface 8. Sheath 16 is constructed f--om a light-transmitting material, such that light waves emitted from light source 10 pass through sheath 16, and illuminate the air passageway 14 of the patient 15. Sheath 16 is selectively fitted on laryngoscope blade 6 in a manner which securely retains the associated portion 26 of sheath 16 closely against the contoured guide surface 8 of laryngoscope blade 6, such that the view along the air passageway 14 of the patient 15 remains wholly unobstructed during insertion of endotracheal tube 12, yet permits the sheath to be manually stripped from laryngoscope blade 6 for disposal after a single use.

The cover 2 is adapted for general use on all common types of laryngoscope blades, and other similar medical and surgical instruments As illustrated in FIG. 1, sheath 16 includes a first portion 56 having a plan shape resembling an elongate finger, and a second portion 58 fanning out from one end of portion 56 and terminating at open end 24. An elongate finger shape is employed for portion 56, in the preferred embodiment, because first portion 56 constitutes that portion of sheath 16 to be conformed to guide surface 8 of blade 6 and a sheath portion having this shape is more easily conformed to laryngoscope blades than sheaths with other shapes. Second portion 58, having a trapezoidal plan shape, illustratively fans out for conveniently covering a significant portion of holder 32, and to facilitate disposal of sheath 16 The fan shape of second portion 58 is easier to slide over handle 32 than is the finger shaped portion 56, and the divergent construction of second portion 58 allows for the insertion of a vacuum source tube under second portion 58 for conforming associated portion 26 of sheath 16. The sheath 16 is illustratively formed of two sheets 30 and 32 of flexible plastic which are heat-sealed along a marginal portion 34 to form closed interior surface 20 (FIG. 5). The open end 24 of sheath 16 is releasably sealed (FIG. 1B) so that interior surface 20 is not contaminated before use, and yet the interior surface 20 can be accessed by blade 6 when application of sheath 16 to the same is desired. Plastic sheets 30 and 32 are constructed from a light-transmitting material allowing light waves from light source 10 to pass through sheath 16 when the same is adheringly conformed to laryngoscope blade 6. Alternatively, sheath 16 could be constructed of a single sheet of flexible light-transmitting plastic through a conventional process of dip-molding. In the preferred embodiment, the interior surface 20 (FIG. 5) of sheath 16 is tacky or self-adherent in order to facilitate retaining sheath 16 in the mentioned conformed shape. The tackiness imparted to interior surface 20 of sheath 16 can be achieved in at least two ways. First, interior surface 20 can be formed from material that is inherently tacky or self adherent due to an electrostatic clinging effect, or the like. Second, interior surface 20 can be coated with an adhesive - possibly during the manufacturing process. Other means are available for adhering the sheath 16 to surfaces 8 and 34. For example, surfaces 8 and 34 may be coated with an adhesive for holding associated portion 26 of sheath 16 thereon subsequent to conforming cover 2 to surfaces 8 and 52. Caution must be taken, however, to insure that the adhesive means employed is only mildly adherent so that sheath 16 can be easily stripped off of blade 6 after use of the same during intubation. It is particularly worth noting that sheath 16 is composed of flexible plastic that can be manipulated to conform with a given surface. By making sheath 16 flexible, the sheath 16 is adaptable to any laryngoscope blade, so that premolding of the sheath 16 is not necessary. Being composed of flexible plastic, sheath 16 can be flattened out so that relatively large quantities of cover 2 can be shipped together, while minimizing bulk. Additionally, the material used to construct sheath 16 must be imperforate to insure that sheath 16 remains sterile during application. In other words, no contaminants should be able to penetrate exterior surface 18 during use of sheath 16 as an instrument cover. Having a simple construction sheath 16 is inexpensive to manufacture, and can be disposed of without undue concern as to expense.

It is necessary to maintain the sterility of sheath 16 prior to use. Contaminating exterior surface 18 of sheath 16 before applying it to laryngoscope blade 6 would defeat the purpose of providing a sterile disposable surface for individual use on a patient 15. Additionally, contamination of sheath 16 could, under some circumstances, transmit undesirable diseases to the patient 15. Therefore, in the preferred embodiment, sheath 16 is maintained in a sterile environment by adhesively mounting the sheath 16 on a cover sheet 50 that is oversized with respect to sheath 16, folding the cover sheet 50 in half so that sheath 16 is enveloped therein, and inserting cover sheet 50 into envelope 52 as illustrated in FIGS. 2 and 3. Cover sheet 50 illustratively consists of a conventional sheet of paper including an exterior surface 51 and interior surface 53. It is necessary that interior surface 53 be sterile so that exterior surface 18 of sheath 16 remain uncontaminated prior to use on patient 15. Envelope 52, which includes two side edges 64, 66, and two ends 68, 70, illustratively consists of two sheets 54 and 55 of conventional paper sealed along side edges 64, 66 and end 68. End 70 is releasably sealed so that cover sheet 50 can be conveniently removed from the envelope 52 without touching the same just prior to use on blade 6. While in the preferred embodiment cover sheet 50 and envelope 52 are composed of conventional paper they could be composed of other materials, such as wax-coated paper, suitable for packaging sheath 16.

Cover 2 is applied to blade 6 by removing cover sheet 50 from envelope 52, unfolding cover sheet 50, making sure not to touch sheath 16 and inserting blade 6 into open end 24 to form hollow cavity 22 of sheath 16, while holding down cover sheet 50 with fingers 48, as illustrated in FIG. 5. Blade 6 and part of handle 32 are ultimately covered by illustratively pulling second portion 58 toward laryngoscope handle 38 until blade end 46 abuts sheath end 74 (FIG. 6). Second portion 58 is subsequently affixed to handle 38 by employment of a retainer 72, which may comprise an elastic band or a piece of tape. When using a piece of tape (not shown), second portion 58 of sheath 16 is taped onto laryngoscope handle 38 near sheath open end 24. Application of retainer 72 to laryngoscope 4 partitions sheath 16 into an interior portion and an exterior portion. The interior portion constitutes that part of sheath 16 sealed off by employment of retainer 72, or, in other words, the portion of sheath 16 disposed along blade 6 and part of holder 32. To conform associated portion 26 of sheath 16 to blade 6 a vacuum source tube 30 is preferably connected to suction end 28 of communication tube 17 to supply suction and evacuate the interior portion partitioned by retainer 72. Since the interior portion partitioned by retainer 72 illustratively encompasses blade 6, and part of holder 32, upon evacuating that part of hollow cavity 22 sealed off by retainer 72, the portion of sheath 16 overlying blade 6 and clamping member 36 is drawn closely against sheath guide surface 8, sheath exterior surface 34, and clamping member 36. Vacuum source tube 30 is connected to a conventional wall source, available in many operating rooms, or some other source, such as a syringe, so that upon applying suction associated portion 26 is pulled down upon blade 6. If an elastic band is used as retainer 72 it is important that the rigidity of communication tube 17 be great enough so that tube 17 will not completely collapse upon application of the retainer 72 to holder 32, and cut off the suction provided by source tube 30. Alternatively a tube connected to a vacuum source may be inserted under sheath 16 in order to effect the conforming process. When employing the preferred conforming method, communication tube 17 can be clamped, subsequent to conformation of associated portion 26 of sheath 16, by a suitable clamping or vacuum retaining device. Upon conforming associated portion 26 to blade 6, a sight line 78 (FIGS. 6 and 7), extending from sighting end 80 to blade end 46 is unimpaired. Addition of retainer 72 further insures that second portion 58 of sheath 16 will not fold over into guide surface 8 during intubation thus impairing sight line 78.

During use of laryngoscope 4 to intubate patient 15, it is necessary that sight line 78 be unimpaired by the cover 2 if intubation is to be successful. By conforming associated portion 26 of sheath 16 to blade 6 and affixing retainer 72 to sheath 16 at holder 32 (FIG. 8), the covered laryngoscope 4 can be applied to patient 15 with little or no awareness of the presence of sheath 16, thus insuring that the typical user of the sheath 16, namely an anesthesiologist or anesthetist, will not find the use of sheath 16 to be distracting during intubation. Of equal import is that the sheath 16, which is composed of light transmitting material, does not impair the use of light source 10 as the user is sighting down guide surface 8 in an attempt to locate the epiglottis of patient 15. Due to the construction of sheath 16, sheath 16 is easily stripped away from laryngoscope 4 subsequent to intubation of patient 15. To strip away sheath 16, second portion 58 of sheath 16 (FIG. 6) is pulled away from laryngoscope 4 so that exterior surface 18 of sheath 16 is inverted, and sheath exterior surface 18 is enveloped within sheath interior surface 20. Inversion of sheath exterior surface 18 ensures that any contaminants present on the same are trapped during the stripping process so that laryngoscope blade 6 remains uncontaminated.

In an alternative embodiment associated portion 26 of sheath 16 is manually conformed to the blade 6. In the alternative embodiment cover 82 comprises sheath 16 packaged in an envelope 84 (FIGS. 9 and 10). Envelope 84 comprises two sterile cover sheets 86, 88 which are releasably sealed along edges 90, 92, 94 and 96. As demonstrated by FIG. 10, the envelope 84 which is flexible, conforms to the shape of sheath 16 and can be stripped along edges 90 and 94 for application onto the laryngoscope blade 6. Illustratively, the sheets 86 and 88 are paper, but other materials such as wax-coated paper, which can be easily stripped away from a plastic sheet, would be suitable for constructing envelope 84.

Cover 82 including envelope 84, with sheath 16 packed therein, is applied to laryngoscope 4 by peeling open sheets 86 and 88 at edge 92 and pulling cover 82 over blade 6 until end portion 46 of blade 6 abuts sheath end 7 (FIG. 11). To manually conform associated portion 26 of sheath 16 to blade 6, fingers 48 are employed to press sheet 86 of envelope 84 into the guide surface 8 and press sheet 88 along exterior surface 34 (FIG. 11). In the alternative embodiment, the closed interior surface 20 of sheath 16 is tacky or self-adherent, as with the preferred embodiment, so that associated portion 26 adheringly conforms to blade 6 by simply pressing the cover 82 against surfaces 8 and 52 with fingers 72. Once cover 82 is conformed to blade 6, envelope 84 is stripped away from sheath 16 as illustrated in FIG. 12. After stripping away envelope 84, a retainer 72, identical to the retainer used in the preferred embodiment is affixed to sheath 16 along handle 38. As envelope 84 is stripped away from blade 6, the associated portion 26 of sheath 16 remains adheringly conformed to guide surface 8 and exterior surface 38, as in the preferred embodiment (FIG. 7) so that, as with the preferred embodiment, sight line 78 remains unimpaired.

Upon conforming associated portion 26 of sheath 16 to blade 6, the covered laryngoscope 4 is ready for use on patient 15 (FIG. 8). After the epiglottis is moved out of the way with covered end portion 46, endotracheal tube 12 is inserted through air passageway 14 of patient 15. The conventional endotracheal tube 12 (not shown) includes an inflatable bulb that is inflated near the larynx upon intubation of the air passageway 14 such that the tube 12 is held securely in the air passageway 14 during the anesthetization of patient 15. After intubating the patient 15 with laryngoscope 4, sheath covered blade 6 is removed from mouth 13, sheath 16 stripped away and discarded as described above. It is particularly noteworthy that the cover 2 is for single use. By its very conception sheath 16 is only exposed to potential contamination for seconds, and once intubation is performed, there is no need for further sterilization. Thus, the user need not concern himself with reusability and the possibility of further contamination subsequent to a single intubation. Expense and effort of resterilizing is saved by the user of cover 2, and the communication of diseases such as AIDS, hepatitis, and herpes during surgery is minimized.

Due to the construction of disposable cover 2, sheath 16 is readily adapted to cover any commonly used laryngoscope blade, no matter what shape the blade may take. Because of its flexibility, sheath 16 provides a universal blade lining that need not be premolded even for most laryngoscope blades possessing unconventional shapes. The flexibility of cover 2 allows the sheath 16 to be pulled over and conformed to blade 6 in a matter of seconds, and because sheath 16 can be closely fitted to any guide surface, the line of sight necessary to effectuate intubation remains unimpaired. Since cover 2 is expressly intended for single use, no resterilization of sheath 16 is required, and the possibility of potential contamination is minimized. Sheath 16 can be compactly packaged in cover 2 to retain its sterility and facilitate convenient shipping. Due to the materials used to construct cover 2, large quantities of covers 2 can be shipped with a minimum amount of bulk.

In the foregoing description, it will be readily appreciated by those skilled in the art that modifications may be made to the invention without departing from the concepts disclosed herein. Such modifications are to be considered as included in the following claims unless these claims by their language expressly state otherwise.

The embodiments of the invention in which an exclusive property or privilege is claimed are defined as follows:

1. In a laryngoscope of the type having an elongate blade with a contoured, channel-shaped guide surface on which an associated light source is mounted to facilitate inserting an endotracheal tube into the air passageway of a patient, the improvement of a disposable cover, comprising:
   a sheath having a sterile exterior surface, and a closed interior surface which defines a hollow cavity shaped to receive therein and envelope said laryngoscope blade; said sheath having an open end through which said laryngoscope blade is inserted into the cavity of said sheath; said sheath being readily flexible to conform an associated portion of the same to the contoured guide surface to said laryngoscope blade, and being constructed from a light-transmitted material, such that light waves emitted from said light source are transmitted through said sheath to illuminate the air passageway of the patient;
   means for selectively fitting said sheath on said laryngoscope blade in a manner which securely retains the associated portion of said sheath closely against the contoured guide surface of said laryngoscope blade, such that the view along the air passageway of the patient remains wholly unobstructed during insertion of the endotracheal tube, yet permits said sheath to be manually stripped from said laryngoscope blade for disposal after a single use; said fitting means including a source of vacuum, means for forming a seal between said sheath and said laryngoscope at a location adjacent to the open end of said sheath, and means for communicating said vacuum source with the cavity of said sheath, whereby applying said vacuum source to said sheath draws the associated portion of said sheath closely against the contoured guide surface of said laryngoscope to define at least a portion of said fitting means.

2. A laryngoscope as set forth in claim 1, wherein: said means for communicating said vacuum source with said sheath includes a tube connected with the interior surface of said sheath, and extending between the open end of said sheath and the cavity portion of said sheath.

3. A laryngoscope as set forth in claim 1, wherein:
   a first portion of said sheath has a plan shape resembling an elongate finger, which is sized so that the first portion of said sheath fits closely over said laryngoscope blade upon insertion of said blade into said sheath.

4. A laryngoscope as set forth in claim 2, including a handle, wherein:
   a second portion of said sheath has a trapezoidal plan shape, which is sized so that the second portion of said sheath fits loosely over said handle and upon pulling the second portion of said sheath away from the laryngoscope subsequent to use on a patient the exterior surface of said sheath is inverted thereby enveloping said exterior surface of said sheath within the interior surface of said sheath thus preventing any contamination of said laryngoscope blade by preventing run-off of contaminants from the exterior surface.

5. A laryngoscope as set forth in claim 4, wherein:
   one of said blade and the associated portion of said sheath interior surface includes an adherent surface which securely holds said sheath against said guide surface to define at least a portion of said fitting means.

6. A laryngoscope as set forth in claim 5, wherein:
   said sheath is constructed from a synthetic resin material having at least one integrally formed tackle surface defining said adherent surface.

7. A laryngoscope as set forth in claim 6, including:
   means for detachably securing the second portion of said sheath around the laryngoscope handle after said blade has been completely inserted into the associated portion of said sheath such that no portion of said sheath can fold back into said guide surface and impair the view of the air passageway of the patient.

8. A laryngoscope as set forth in claim 7, including a neck portion on the laryngoscope handle wherein:
   said detachable securing means comprises an elastic band secured around said neck portion, whereby said band can be easily removed from said neck portion prior to stripping away said sheath from said laryngoscope.

9. A laryngoscope as set forth in claim 7, wherein:
   said detachable securing means comprises a piece of adhesive tape attached to the laryngoscope handle and the second portion of said sheath, whereby said tape can be easily removed from the handle prior to stripping away said sheath from said laryngoscope.

10. A laryngoscope as set forth in claim 7, further comprising:
    a sterile cover sheet, that is oversized with respect to said sheath, upon which a part of said sheath exterior surface is mounted on so that said sheath is enveloped in the cover sheet upon folding the cover sheet over at least once;
    an envelope into which said folded cover sheet is inserted;
    said envelope including a releasably sealed edge whereby said sheath is applied to the laryngoscope blade by removing said sterile cover sheet enveloping said sterile sheath from the envelope, unfolding said sterile cover sheet, and inserting the laryngoscope blade into said open end of said sheath.

11. A laryngoscope as set forth in claim 7, further comprising:
    a sterile disposable envelope in which said sheath is enclosed, including a releasably sealed end juxtaposed with said open end of said sheath to facilitate insertion of said blade therein such that opening of said envelope end exposes the open end of said sheath; said envelope being flexible to permit said envelope and the associated portion of said sheath to be contemporaneously manually conformed to the contoured guide surface of said laryngoscope blade without contaminating said sheath by touching the same.

12. A laryngoscope as set forth in claim 1 wherein: said sheath is constructed from a synthetic resin material having at least one integrally formed tacky surface defining said adherent surface.

13. A laryngoscope as set forth in claim 1 further comprising:

a sterile cover sheet, that is oversized with respect to said sheath, upon which a part of said sheath exterior surface is mounted so that said sheath is enveloped in the cover sheet upon folding the cover sheet over is least once;

an envelope into which said folded cover sheet is inserted;

said envelope including a releasably sealed edge whereby said sheath is applied to the laryngoscope blade by removing said sterile cover sheet enveloping said sterile sheath from the envelope, unfolding said sterile cover sheet, and inserting the laryngoscope blade into said open end of said sheath.

14. A disposable cover for laryngoscopes of the type having an elongate blade with a contoured, channel-shaped guide surface on which an associated light source is mounted to facilitate inserting an endotracheal tube into the air passageway of a patient; said cover comprising:

a sheath having a sterile exterior surface, and a closed interior surface which defines a hollow cavity originally of a different three-dimensional shape than the shape of laryngoscope blades which it is intended to cover, said cover being adapted to receive and envelope a laryngoscope blade; said sheath having an open end adapted for insertion of a laryngoscope blade into the cavity of said sheath; said sheath being readily flexible and formable to conform an associated portion of the same to the shape of a contoured guide surface of a laryngoscope blade, and being constructed from a light-transmitting material, such that light waves emitted from the light source are transmitted through the sheath to illuminate an air passageway of a patient;

retaining means for securely retaining the associated portion of said sheath closely against a contoured guide surface of laryngoscope blade, after selectively fitting said sheath on a laryngoscope blade, such that a view along an air passageway of the patient remains wholly unobstructed during insertion of an endotracheal tube, yet permits said sheath to be manually stripped from a laryngoscope blade for disposal after a single use;

means for forming a seal between said sheath and a laryngoscope at a location adjacent to the open end of said sheath; and a tube connected with the interior surface of said sheath, and having an outer end disposed exterior to said seal means, and an inner end disposed within said sheath cavity interior to said seal means, whereby applying suction to the outer end of said tube evacuates the cavity of said sheath, and draws said sheath closely against a laryngoscope blade to define at least a portion of said retaining means.

15. A cover as set forth in claim 16 wherein: Applicant: William M. Slater Serial No.: 07/072,600 Page :7 said sheath is constructed from a synthetic resin material having at least one integrally formed tacky surface defining said adherent surface.

16. A cover as set forth in claim 15 further comprising:

a sterile cover sheet, that is oversized with respect to said sheath, upon which a part of said sheath exterior surface is mounted so that said sheath is enveloped in the cover sheet upon folding the cover sheet over at least once;

an envelope into which said folded cover sheet is inserted;

said envelope including a releasably sealed edge whereby said sheath can be applied to a laryngoscope blade by removing from the envelope said sterile cover sheet enveloping said sterile sheath, unfolding said sterile cover sheet, and inserting a laryngoscope blade into said open end of said sheath.

17. A method for rendering sterile a laryngoscope blade of the type having a contoured, channel-shaped guide surface on which an associated light source is mounted to facilitate inserting an endotraceal tube into the air passageway of a patient; said method comprising:

providing a sheath having an exterior surface, and a closed interior surface which defines a hollow cavity shaped to receive the laryngoscope blade through an open end thereof; the sheath being readily flexible to conform an associated portion of the same to the contoured guide surface of the laryngoscope blade, and being constructed from a light-transmitting material, such that light waves emitted from the light source are transmitted through the sheath to illuminate the air passageway of the patient;

sterilizing the exterior surface of the sheath;

inserting the laryngoscope blade through the open end of said sheath and into the hollow cavity thereof without contaminating the exterior surface of the sheath;

conforming the associated portion of the sheath to the contoured guide surface of the laryngoscope blade; the associated portion of the sheath closely against the guide surface of the laryngoscope blade, such that the view along the air passageway of the patient remains wholly unobstructed during insertion of the endotracheal tube, yet permits the sheath to be stripped from the laryngoscope blade for disposal after a single use, and wherein said sheath conforming and sheath retaining steps comprise:

forming a substantially airtight seal between the sheath and a selected portion of a laryngoscope associated with the laryngoscope blade at a location disposed adjacent to the open end of said sheath;

providing a source of vacuum;

communicating the source of vacuum with the hollow interior of said sheath when said sheath is positioned over said laryngoscope blade, whereby the vacuum collapsed the sheath about the laryngoscope blade and securely retains the same in place.

18. A method as set forth in claim 17 wherein said sheath conforming and sheath retaining steps further comprise:

providing a tube attached to said sheath interior surface between the open end of said sheath and a point adjacent to the associated portion of said sheath;

communicating the source of vacuum with the hollow interior of said sheath when said sheath is positioned over said laryngoscope blade by connecting said vacuum source to the communicating tube at the end of the tube disposed adjacent to the open end of said sheath.

19. A method as set forth in claim 18 including:

providing a cover sheet with at least one sterile surface, said cover sheet being oversized with respect to said sheath;

centrally mounting a portion of said sheath exterior surface on the sterile surface of said cover sheet after said sterilizing step;

folding the cover sheet so that said sheath is enveloped within the sterile surface of said cover sheet;

providing an envelope for said folded cover sheet;

inserting said folded cover sheet in the envelope and releasably sealing the envelope at one edge to indefinitely maintain the sterility of the sheath.

20. A method as set forth in claim 19, further comprising:

providing a sheath including a first portion having an elongate finger plan shape, which is sized to fit closely over the blade of said laryngoscope, and a second portion, having a trapezoidal plan shape, which is sized to fit loosely over a handle associated with the laryngoscope blade;

stripping said sheath off of the laryngoscope subsequent to use on the patient by pulling the second portion of said sheath away from the laryngoscope causing the exterior surface of said sheath to be inverted thereby enveloping the exterior surface of said sheath thus preventing any contamination of said laryngoscope blade by preventing run-off of contaminates from the exterior surface.

21. A method as set forth in claim 17 including:

providing a sterile envelope for said sheath;

positioning said sheath in said envelope after said sterilizing step; and sealing said envelope to indefinitely maintain the sterility of the sheath.

* * * * *

UNITED STATES PATENT AND TRADEMARK OFFICE
CERTIFICATE OF CORRECTION

PATENT NO. : 4,878,486

DATED : November 7, 1989

INVENTOR(S) : William M. Slater

It is certified that error appears in the above-identified patent and that said Letters Patent is hereby corrected as shown below:

Column 2, Line 43:
   "insrting" should be --inserting--;
Column 2, Line 56:
   "readilY" should be --readily--;
Column 2, Line 57:
   "larYngoscope" should be --laryngoscope--;

Column 5, Line 24:
   "f--om" should be --from--;
Column 5, Line 52:
   After "sheath 16" insert --.--;
Column 7, Line 66:
   After "4" delete -- - --;
Column 8, Line 21:
   "end 7" should be --end 74--;
Column 9, Claim 1, Line 35, after "surface":
   "to" should be --of--;
Column 10, Claim 6, Line 24:
   "tackle" should be --tacky--;
Column 11, Claim 13, Line 17:
   "is" should be --at--;
Column 11, Claim 15, Line 67:
   "claim 16" should be --claim 14--;
Columns 11, Claim 15, Lines 67 and 68:
   After "wherein" delete --Applicant:
   William M. Slater Serial No. 07/072,600
   Page:7--;

UNITED STATES PATENT AND TRADEMARK OFFICE
CERTIFICATE OF CORRECTION

PATENT NO. : 4,878,486

DATED : November 7, 1989

INVENTOR(S) : William M. Slater

It is certified that error appears in the above-identified patent and that said Letters Patent is hereby corrected as shown below:

Column 12, Claim 17, Line 63:
 "collapsed" should be --collapses--;
Column 13, Claim 18, Line 9:
 "the" (first occurrence) should be --that--.

Signed and Sealed this

Twenty-eighth Day of May, 1991

*Attest:*

HARRY F. MANBECK, JR.

*Attesting Officer*  *Commissioner of Patents and Trademarks*